United States Patent
Bornscheuer et al.

(10) Patent No.: US 6,365,398 B1
(45) Date of Patent: Apr. 2, 2002

(54) PROCESS FOR PREPARATION TO STEREOISOMERIC CARBOXYLIC ACID ESTERS

(75) Inventors: Uwe Bornscheuer, Greifswald; Erik Henke, Stuttgart, both of (DE); Hong Yang, Canberra (AU)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/505,709

(22) Filed: Feb. 17, 2000

(30) Foreign Application Priority Data

Feb. 25, 1999 (DE) .......................................... 199 08 074

(51) Int. Cl.[7] ................................................. C12P 41/00
(52) U.S. Cl. ...................................................... 435/280
(58) Field of Search .......................................... 435/280

(56) References Cited

U.S. PATENT DOCUMENTS 4,963,492 A * 10/1990 Keller et al. ................ 435/280

OTHER PUBLICATIONS

Fowler et al., "Highly Diastereoselective Inter-esterification Reactions Involving a Racemic Acetate and a Racemic Carboxylic Acid actalysed by Lipase Enzymes", J. Chem. Soc. Chem. Commun. 1991 (7): 433–5.*

Theil et al., "Double Enantioselection'by a Lipase-Catalyzed Transesterification of a meso-Diol with a Racemic Carboxylic Ester", Tetrahedron Letters, 33 (24): 3457–60 (1992).*

Yang et al., "Highly Efficient Double Enantioselection by Lipase-Catalyzed Transesterification of (R,S)-Carboxylic Acid Vinyl Esters with (RS)-1-phenylethanol", TetrahedronA:Symmetry 10 (5): 967–60 (1999).*

Yamazaki et al., "Diametric Stereselectivity of Pseudomonas fluorescens Lipase and Candida cylindracea Lipase in the Acylation of Organometallic Alcohols", Agric. Biol. Chem. 54 (12): 3357–61 (1990).*

* cited by examiner

Primary Examiner—Sandra E. Saucier
(74) Attorney, Agent, or Firm—Keil & Weinkauf

(57) ABSTRACT

The present invention relates to a process for the preparation of stereoisomeric carboxylic acid esters consisting of an acid and of an alcohol component each having at least one chiral center, at least one stereoisomer of the carboxylic acid ester being present in an excess, by reacting a racemic carboxylic acid ester with a racemic alcohol in the presence of a carboxyl ester hydrolase (EC 3.1.1).

7 Claims, No Drawings

PROCESS FOR PREPARATION TO STEREOISOMERIC CARBOXYLIC ACID ESTERS

BACKGROUND OF THE INVENTION

The invention relates to a process for the preparation of stereoisomeric carboxylic acid esters consisting of an acid and an alcohol component each having at least one chiral center, at least one stereoisomer of the carboxylic acid ester being present in an excess.

Stereoisomerically pure carboxylic acid esters having at least two chiral centers are important precursors of biologically active substances, such as natural substances, drugs and crop protection agents. An economical preparation process is therefore of great importance.

It is known to prepare optically pure alcohols by transesterification of the racemic alcohols using achiral alkyl carboxylates in an organic solvent in the presence of carboxyl esterases (Klibanov et al., J. Am. Chem. Soc. 1984, 106, 2687–2692). To increase the reaction rate and to shift the reaction equilibrium, it has proven very useful to employ activated achiral carboxylic acid esters, in particular enol esters, oxime esters or anhydrides. Frequently employed acyl donors are vinyl esters and, among these, especially vinyl acetates (see Degueil-Castaing et al., Tetrahedron Lett., 1987, 28, 953–954; Wang et al., J. Am. Chem. Soc., 1988, 110, 7200–7205; Laumen et al., J. Chem. Soc., Chem. Commun., 1988, 1459–1461), oxime esters and, among them, especially 2-propanoneoximyl acetate and cyclohexanoneoximyl acetate (A. Ghogare, G. S. Kumar, J. Chem. Soc., Chem. Commun. 1989, 1533–1535; J. Chem. Soc., Chem. Commun. 1990, 134–135) or anhydrides (D. Bianchi, P. Cesti, E. Battistel, J. Org. Chem. 1988, 53, 5531–5534; J. H. Xu, T. Kawamoto, A. Tanaka, Appl. Microbiol. Biotechnol. 1995, 43, 639–643).

It is furthermore known to prepare optically active carboxylic acids by reacting their racemic esters with achiral alcohols in organic solvents in the presence of lipases (see Holmberg et al., Appl. Microbiol. Biotechnol., 1992, 35, 572–578; Persichetti et al., Tetrahedron Lett., 1996, 37, 6507–6510; Ozegowski et al., Liebigs Ann. 1994, 215–217).

It is furthermore known to prepare stereoisomerically enriched amides by reacting racemic ethyl 2-chloropropionate with racemic amines in the presence of lipases (R. Brieva, J. Chem. Soc., Chem. Commun. 1990, 1386–1387).

It is furthermore known to prepare a mixture of four stereoisomeric esters by reaction of a meso-diol with racemic 2,2,2-trifluoroethyl 2-chloropropanate in organic solvents in the presence of a lipase (F. Theil et al., Tetrahedron Lett. 1992, 33, 3457–3460). The process has the disadvantage that although the reaction times are short only low diastereomer excesses (3.6% de to 51.5% de) are achieved.

The preparation of stereoisomerically enriched carboxylic acid esters by conversion of racemic carboxylic acids using racemic alcohols in organic solvents in the presence of a lipase is known from two publications: P. W. Fowler et al. describe the reaction of racemic p-chlorophenoxypropanoic acid with a racemic bicycloheptenol (J. Chem. Soc., Chem. Commun. 1991, 453–454). The process has the disadvantage that although the diastereomer excesses are higher (16% de to 72% de), in spite of high reaction times only a low conversion and a low enantioselectivity (E(alcohol)=5.8 to 26.7; E(carboxylic acid)=1.3 to 15.7) are achieved, E being understood as meaning the enantioselectivity as defined by Sih et al. (J. Am. Chem. Soc. 1982, 104, 7294–7299). Although the use of the acetylated racemic bicycloheptenol leads to an increase in selectivity, in spite of still greater reaction times even lower conversions are achieved. Chen et al. describe the reaction of racemic, chlorinated phenoxypropionic acids with racemic phenylalkanols. The process has the disadvantage that in spite of high reaction times only low conversions and, apart from one exception (E(acid)=108), only low enantioselectivities E(alcohol)=1.0 to 13.6; E(carboxylic acid)=2.1 to 35.6) are achieved. Therefore only low diastereoselectivities are also achieved.

An optimal and economic enzyme-catalyzed preparation of stereoisomeric carboxylic acid esters consisting of an acid and an alcohol component each having at least one chiral center should advantageously fulfil a number of conditions, such as, for example, 1. a high enantioselectivity, in each case based on the acid and alcohol components,
2. a high diastereoselectivity,
3. good space-time yield (short reaction times, high conversions based on one enantiomer, high starting material and product concentrations),
4. high substrate spectrum of the enzyme,
5. high chemical yield of the desired product,
6. low amounts of catalyst (amounts of enzyme),
7. easy purification of the synthesis products,
8. good solubility of starting material and product under the reaction conditions,
9. inexpensive synthesis (easily preparable starting materials, good handleability of the starting materials, solvents, reagents and enzymes).

The object of the present invention is therefore to remedy the outlined deficiencies of the prior art and to provide an improved process which as much as possible fulfils the conditions described above.

BRIEF SUMMARY OF THE INVENTION

Accordingly, we have found that this object is achieved by a process for the preparation of stereoisomeric carboxylic acid esters, consisting of a carboxylic acid and an alcohol component each having at least one chiral center, at least one stereoisomer of the carboxylic acid ester being present in an excess, in which a racemic carboxylic acid ester is reacted with a racemic alcohol in the presence of a carboxyl ester hydrolase (EC 3.1.1) (Enzyme Nomenclature 1992, NC-IUBMB, Academic Press, Inc., San Diego). The preparation of the stereoisomeric carboxylic acid ester, where at least one stereoisomer of the carboxylic acid ester is present in an excess, is thus carried out by transesterification of a racemic carboxylic acid ester with a racemic alcohol in the presence of a carboxyl ester hydrolase (EC 3.1.1).

DETAILED DESCRIPTION OF THE INVENTION

The process according to the invention leads to an advantageous increase in the reaction rate and the conversion with a simultaneous increase in the enantioselectivity and the diastereoselectivity of the enzymes used (carboxyl ester hydrolases). High diastereomer excesses and enantioselectivities can thus be achieved with high reaction conversions and short reaction times.

At about 50% conversion, diastereomer excesses of at least 50% de, preferably at least 55% de, are achieved. The enantioselectivity (E) for the alcohol is advantageously at least 30, preferably 80, particularly preferably greater than 100. Stereoisomeric carboxylic acid esters consisting of a carboxylic acid and an alcohol component each having at least one chiral center are understood as meaning all possible stereoisomers of a carboxylic acid ester, the carboxylic acid and the alcohol component in each case containing at least one chiral center.

At least one chiral center is understood as meaning 1 to 3, preferably 1 or 2 chiral centers, particularly preferably 1 chiral center for the carboxylic acid and the alcohol component in each case. For $i$ chiral centers in the total molecule of the carboxylic acid ester, $2^i$ possible stereoisomers of the carboxylic acid ester result.

Accordingly, the racemic carboxylic acid ester and the racemic alcohol each have at least one chiral center. In principle, racemic alcohols and racemic carboxylic acid esters which each have at least one chiral center with a large structural breadth are accessible to the process according to the invention.

In a preferred embodiment of the process, the racemic carboxylic acid ester used is an activated racemic carboxylic acid ester. An activated racemic carboxylic acid ester is understood as meaning a racemic carboxylic acid ester which contains one component with a hydroxyl group as a leaving group which has better leaving group properties than ethanol in the transfer of the racemic acyl group (acid components) of the racemic carboxylic acid ester to an alcohol. The leaving group of the activated racemic carboxylic acid ester accordingly has a lower nucleophilicity than ethanol. By way of example, activated racemic carboxylic acid esters which may be mentioned are racemic carboxylic acid haloalkyl esters, such as carboxylic acid trichloroethyl esters or carboxylic acid trifluoroethyl esters or racemic carboxylic acid haloaryl esters such as carboxylic acid pentachlorophenyl esters or anhydrides, in the case of anhydrides the corresponding racemic carboxylic acid being the leaving group.

Activated racemic carboxylic esters are also understood as meaning racemic carboxylic acid esters in which the leaving group rearranges after liberation or in another way is no longer available to the equilibrium reaction as a reactant, so that the back reaction is suppressed and the equilibrium is steered in the desired direction.

By way of example, activated racemic carboxylic acid esters which may be mentioned are racemic carboxylic enol esters, such as carboxylic acid vinyl esters, carboxylic acid (1-methyl)vinyl esters, carboxylic acid (1-ethyl)vinyl esters, carboxylic acid (1-propyl)vinyl esters or carboxylic acid (1-butyl)vinyl esters or racemic oxime esters, such as carboxylic acid 2-propaneoximyl esters or carboxylic acid cyclohexanoneoximyl esters. Preferably, the activated racemic carboxylic acid esters used are racemic carboxylic acid enol esters, in particular carboxylic acid vinyl esters or racemic carboxylic acid (1-methyl)vinyl esters.

In a preferred embodiment of the process according to the invention, the acid and the alcohol components of the stereoisomeric carboxylic acid ester and accordingly of the racemic carboxylic acid ester and the racemic alcohol each have a chiral center. Accordingly, on account of the two chiral centers four possible stereoisomers of the carboxylic acid ester (R,R), (S,S), (R,S) and (S,R) result in the total molecule of the stereoisomeric carboxylic acid (in each bracket the first letter indicates the absolute configuration (according to Cahn-Ingold-Prelog) of the chiral center of the carboxylic acid component and the second letter the absolute configuration of the chiral center of the alcohol component), at least one, in this case preferably one, stereoisomer being formed in an excess (doubled enantioselectivity). Excess of a stereoisomer is understood in this case as meaning when the proportion of the stereoisomer in the stereoisomer mixture is greater than 25% (molar ratio). Diastereomer excess is understood in this case as meaning the excess of the total of the proportions of the (R,R) and of the (S,S) stereoisomer compared with the total of the proportions of the (S,R) and of the (R,S) stereoisomer or of the excess of the total of the proportions of the (S,R) and of the (R,S) stereoisomer compared with the total of the proportions of the (R,R) and of the (S,S) stereoisomer, depending on which stereoisomer is present in an excess.

In a particularly preferred embodiment of the process according to the invention, stereoisomeric carboxylic acid esters of the general formula I

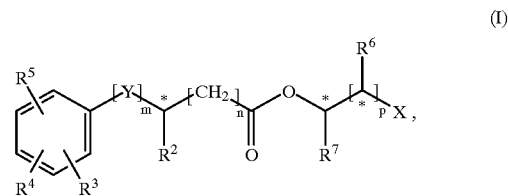

(I)

where the substituents and variables have the meanings

* is a possible chiral center, n, m, p independently of one another are 0 or 1,

X is an unsubstituted or F—, Cl—, Br—, I—, $N_2$— or $C_1$–$C_4$-alkoxy-substituted $C_1$–$C_{10}$-alkyl, $C_2$–$C_{10}$-alkenyl, $C_2$–$C_{10}$-alkynyl or $C_3$–$C_8$-cycloalkenyl, $C_6$–$C_{14}$-aryl, $C_7$–$C_{16}$-alkylaryl, $C_8$–$C_{16}$-alkenylaryl, $C_8$–$C_{16}$-alkynylaryl, $C_7$–$C_{18}$-arylalkyl, $C_8$–$C_{18}$-arylalkenyl, $C_8$–$C_{18}$-arylalkynyl or $C_4$–$C_{12}$-heteroaryl radical or a substituted $C_6$–$C_{14}$-aryl, $C_7$–$C_{16}$-alkylaryl, $C_8$–$C_{16}$-alkenylaryl, $C_8$–$C_{16}$-alkynylaryl, $C_7$–$C_{18}$-arylalkyl, $C_8$–$C_{18}$-arylalkenyl, $C_8$–$C_{18}$-arylalkynyl or $C_4$–$C_{12}$-heteroaryl radical, where in each case two adjacent aryl substituents can together form a further substituted or unsubstituted aromatic, saturated or partially saturated ring having 5 to 6 atoms in the ring, which can contain one or more heteroatoms such as O, N or S, Y is —$CH_2$—, —CO—, oxygen or sulfur, $R^2$ is a substituted or unsubstituted, branched or unbranched $C_1$–$C_6$-alkyl, $C_1$–$C_4$-alkoxy, $C_3$–$C_6$-cycloalkyl, $C_6$–$C_{14}$-aryl or $C_4$–$C_{12}$-heteroaryl radical, $R^3$, $R^4$, $R^5$ independently of one another are hydrogen, a hydroxyl, halogen, cyano, nitro or amino radical or a substituted or unsubstituted, branched or unbranched $C_1$–$C_{10}$-alkyl, $C_2$–$C_{10}$-alkenyl, $C_2$–$C_{10}$-alkynyl, $C_1$–$C_{10}$-alkoxy, $C_2$–$C_{10}$-alkenyloxy, $C_2$–$C_{10}$-alkynyloxy, $C_3$–$C_{10}$-cycloalkyl, $C_3$–$C_{10}$-cycloalkyloxy, $C_6$–$C_{14}$-aryl, $C_7$–$C_{18}$-alkylaryl, $C_4$–$C_{12}$-heteroaryl or $C_5$–$C_{16}$-alkylheteroaryl radical or a substituted or unsubstituted olefinic or aromatic acyl radical or two adjacent substituents $R^3$, $R^4$ and $R^5$ can together form a further substituted or unsubstituted aromatic, saturated or partially saturated ring having 5 to 6 atoms, which can contain one or more heteroatoms such as O, N or S, $R^6$ is hydrogen or a substituted or unsubstituted, branched or unbranched $C_1$–$C_6$-alkyl, $C_1$–$C_4$-alkoxy, $C_3$–$C_6$-cycloalkyl, $C_6$–$C_{14}$-aryl or $C_4$–$C_{12}$-heteroaryl radical and R⁷ is hydrogen or a substituted or unsubstituted, branched or unbranched $C_1$–$C_6$-alkyl, $C_1$–$C_4$-alkoxy or $C_3$–$C_6$-cycloalkyl radical, where in the case where p=0, $R^7$ is not hydrogen or X and in the case where p=1, either $R^6$ or $R^7$ is hydrogen, but not both are simultaneously hydrogen and in the case where $R^7$=hydrogen, $R^6$ is not X and in the case where $R^7$ is not hydrogen, $R^6$ is hydrogen or X, are prepared by reacting a racemic carboxylic acid ester of the general formula II

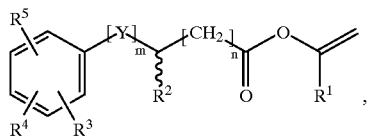

(II)

where
$R^1$ is hydrogen or $C_1$–$C_4$-alkyl,
with a racemic alcohol of the general formula III

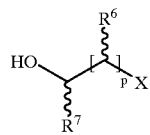

(III)

in the presence of a carboxyl ester hydrolase (EC 3.1.1).

The possible chiral centers marked by * can be present independently of one another either in the R or S configuration (according to Cahn-Ingold-Prelog). In this particularly preferred embodiment of the process according to the invention, the racemic carboxylic acid esters of the formula II and the racemic alcohols of the formula III and thus also the acid and alcohol components in each case of the stereoisomeric carboxylic acid esters of the formula I, as mentioned above, in each case only have one chiral center.

The variables n, m and p independently of one another are 0 or 1. In order to achieve the presence of only one chiral center in the alcohol component of the stereoisomeric carboxylic acid ester of the formula I, it applies in the case p=0 that $R^7$ is not hydrogen or X and in the case p=1 that either $R^6$ or $R^7$ is hydrogen, but not both are simultaneously hydrogen and in the case where $R^7$ is hydrogen, $R^6$ is not X and in the case where $R^7$ is not hydrogen, $R^6$ is hydrogen or X. X is understood as meaning the following radicals, which are unsubstituted or substituted by F, Cl, Br, I, $NO_2$ or $C_1$–$C_4$-alkoxy, such as methoxy, ethoxy, propoxy, isopropoxy, n-butoxy, sec-butoxy or t-butoxy, preferably methoxy:

$C_1$–$C_{10}$-alkyl radicals, such as, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, n-hexyl, n-heptyl, n-octyl, n-nonyl, n-decyl, preferably ethyl,
propyl or butyl or $C_2$–$C_{10}$-alkenyl radicals, such as, for example, vinyl, 1-propenyl, 1-butenyl, 1-pentenyl, 1-hexenyl, 1-heptenyl, 1-octenyl, 1-nonenyl, 1-decenyl, 2-chlorovinyl, 3-chloro-1-propenyl, 4-chloro-1-butenyl, 5-chloro-1-pentenyl, 6-chloro-1-hexenyl, 7-chloro-1-heptenyl, 8-chloro-1-octenyl, 9-chloro-1-nonenyl, 10-chloro-1-decenyl, 2-nitrovinyl, 3-nitro-1-propenyl, 4-nitro-1-butenyl, 5-nitro-1-pentenyl, 6-nitro-1-hexenyl, 7-nitro-1-heptenyl, 8-nitro-1-octenyl, 9-nitro-1-nonenyl or 10-nitro-1-decenyl, preferably vinyl, 1-propenyl, 1-butenyl, 1-pentenyl or 1-hexenyl or $C_2$–$C_{10}$-alkynyl radicals, such as, for example ethynyl, 1-propynyl, 1-butynyl, 1-pentynyl, 1-hexynyl, 1-heptynyl, 1-octynyl, 1-nonynyl, 1-decynyl, 2-chlorovinyl, 3-chloro-1-propynyl, 4-chloro-1-butynyl, 5-chloro-1-pentynyl, 6-chloro-1-hexynyl, 7-chloro-1-heptynyl, 8-chloro-1-octynyl, 9-chloro-1-nonynyl, 10-chloro-1-decynyl, 2-nitrovinyl, 3-nitro-1-propynyl, 4-nitro-1-butynyl, 5-nitro-1-pentynyl, 6-nitro-1-hexynyl, 7-nitro-1-heptynyl, 8-nitro-1-octynyl, 9-nitro-1-nonynyl or 10-nitro-1-decynyl, preferably ethynyl, 1-propynyl, 1-butynyl, 1-pentynyl or 1-hexynyl or $C_3$–$C_8$-cycloalkenyl radicals, such as, for example cyclopropenyl, cyclobutenyl, cyclopentenyl, cyclohexenyl, cycloheptenyl, cyclooctenyl, preferably cyclopentenyl or cyclohexenyl or $C_6$–$C_{14}$-aryl radicals, such as, for example phenyl, naphthyl, anthracyl, phenanthryl, p-nitrophenyl, o-nitrophenyl, m-nltrophenyl, p-chlorophenyl, o-chlorophenyl, m-chlorophenyl, 2,4-dichlorophenyl, 2,3-dichlorophenyl, 3,5-dichlorophenyl, 3,4-dichlorophenyl, 2,4-dimethoxyphenyl, 2,3-dimethoxyphenyl, 3,5-dimethoxyphenyl, 3,4-dimethoxyphenyl, 2-chloro-4-nitrophenyl, p-methoxyphenyl, o-methoxyphenyl, m-methoxyphenyl or 6-methoxy-2-naphthyl, preferably phenyl, p-nitrophenyl, p-chlorophenyl or 6-methoxy-2-naphthyl or $C_7$–$C_{16}$-alkylaryl radicals, such as, for example benzyl, p-chlorobenzyl, p-nitrobenzyl, p-methoxybenzyl, 2-phenylethyl, 3-phenylpropyl, 2-(p-nitrophenyl)ethyl, 2-(p-chlorophenyl)ethyl or 2-(p-methoxyphenyl)ethyl, preferably benzyl, p-chlorobenzyl or p-methoxybenzyl or $C_8$–$C_{16}$-alkenylaryl radicals, such as, for example 2-phenylvinyl, 2-(p-nitrophenyl)vinyl, 2-(p-chlorophenyl)vinyl or 2-(p-methoxyphenyl)vinyl or 2-benzylvinyl, preferably 2-phenylvinyl or $C_8$–$C_{16}$-alkynylaryl radicals, such as, for example 2-phenylethynyl, 2-(p-nitrophenyl)ethynyl, 2-(p-chlorophenyl)-ethynyl or 2-(p-methoxyphenyl)ethynyl, preferably 2-phenylethynyl or $C_7$–$C_{18}$-arylalkyl radicals, such as, for example p-methylphenyl, p-ethylphenyl, p-propylphenyl, p-isopropylphenyl, p-t-butylphenyl, o-methylphenyl, o-ethylphenyl, o-propylphenyl, o-isopropylphenyl, o-t-butylphenyl, 4-chloro-2-methylphenyl or 4-methoxy-2-methylphenyl, preferably p-methylphenyl or $C_8$–$C_{18}$-arylalkenyl radicals, such as, for example, p-vinylphenyl, or $C_8$–$C_{18}$-arylalkynyl radicals, such as, for example, p-ethynylphenyl, or $C_4$–$C_{12}$-heteroaryl radicals, such as, for example, furyl, thienyl, pyrrolyl, pyridyl, pyrimidyl, pyrazinyl, imidazolyl, oxazolyl, thiazolyl, indolyl, 2-(4-chloro) thienyl, preferably furyl, thienyl, pyrrolyl, pyridyl.

Furthermore, X is understood as meaning a substituted $C_6$–$C_{14}$-aryl, $C_7$–$C_{16}$-alkylaryl, $C_8$–$C_{16}$-alkenylalkyl, $C_8$–$C_{16}$-alkynylaryl, $C_7$–$C_{18}$-arylalkyl, $C_8$–$C_{18}$-arylalkenyl, $C_8$–$C_{18}$-arylalkynyl or $C_4$–$C_{12}$-heteroaryl radical, where two adjacent aryl substituents in each case can together form a further substituted or unsubstituted aromatic, saturated or partially saturated ring having 5 to 6 atoms in the ring, which can contain one or more heteroatoms such as O, N or S. The following structures may be listed by way of example, the linkage sites being marked by a bonding dash:

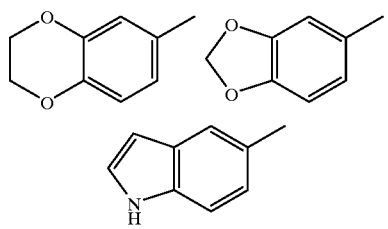

$R^2$ is a substituted or unsubstituted, branched or unbranched $C_1$–$C_6$-alkyl, $C_3$–$C_6$-cycloalkyl, $C_1$–$C_4$-alkoxy, $C_6$–$C_{14}$-aryl or $C_4$–$C_{12}$-heteroaryl radical.

Unsubstituted, branched or unbranched $C_1$–$C_6$-alkylreste for $R^2$ which may be mentioned are, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl. Methyl, ethyl, n-propyl, n-butyl, i-propyl and i-butyl are preferred. Substituted $C_1$–$C_6$-alkyl radicals which may be mentioned by way of example are the corresponding substituted $C_1$–$C_6$-alkyl radicals having the substituents described below.

Unsubstituted, branched or unbranched $C_3$–$C_6$-cycloalkyl radicals for $R^2$ which may be mentioned are, for example cyclopropyl, cyclobutyl, cyclopentyl, cyclohexyl, 1-methylcyclopropyl, 1-ethylcyclopropyl or 1-propylcyclopropyl. The cycloalkyl radicals can also contain heteroatoms such as S, N and O in the ring. Substituted $C_3$–$C_6$-cycloalkyl radicals which may be mentioned by way of example are the corresponding substituted $C_3$–$C_6$-cycloalkyl radicals having the substituents described below.

Unsubstituted, branched or unbranched $C_1$–$C_4$-alkoxy radicals for $R^2$ which may be mentioned are, for example, methoxy, ethoxy, propoxy, isopropoxy, n-butoxy, sec-butoxy or t-butoxy, preferably methoxy. Substituted $C_1$–$C_4$-alkoxy radicals which may be mentioned by way of example are the corresponding substituted $C_1$–$C_4$-alkoxy radicals having the substituents described below.

Unsubstituted or substituted $C_6$–$C_{14}$-aryl radicals or $C_4$–$C_{12}$-heteroaryl radical for $R^2$ which may be mentioned are the $C_6$–$C_{14}$-aryl radicals and the $C_4$–$C_{12}$-heteroaryl radicals described by way of example, preferably phenyl, naphthyl, p-chlorophenyl, p-methoxyphenyl or furyl.

Substituents of the radicals of $R^2$ mentioned are, for example, one or more substituents such as halogen, such as fluorine, chlorine or bromine, or cyano, nitro, amino or hydroxyl. Methyl, chlorine and hydroxyl are preferred.

$R^3$, $R^4$, $R^5$ independently of one another are hydrogen or a hydroxyl, cyano, nitro, amino or halogen radical, such as fluorine, chlorine, bromine or iodine, or a substituted or unsubstituted, branched or unbranched $C_1$–$C_{10}$-alkyl, $C_2$–$C_{10}$-alkenyl, $C_2$–$C_{10}$-alkynyl, $C_1$–$C_{10}$-alkoxy, $C_2$–$C_{10}$-alkenyloxy, $C_2$–$C_{10}$-alkynyloxy, $C_3$–$C_{10}$-cycloalkyl, $C_3$–$C_{10}$-cycloalkyloxy, $C_4$–$C_{14}$-aryl, $C_7$–$C_{18}$-alkylaryl, $C_4$–$C_{12}$-hetaryl- or $C_5$–$C_{16}$-alkylheteroaryl radical or a substituted or unsubstituted olefinic or aromatic acyl radical. Furthermore, two adjacent substituents $R^3$, $R^4$ and $R^5$ can together form a further substituted or unsubstituted aromatic, saturated or partially saturated ring having 5 to 6 atoms in the ring, which can contain one or more heteroatoms such as O, N or S. In this case, fused systems can be formed where not more than one ring can be fused to the central ring, such as substituted or unsubstituted naphthyl. Possible substituents in this case are preferably halogen radicals, such as fluorine, bromine or iodine, or $C_1$–$C_4$-alkoxy radicals, such as methoxy, ethoxy, n-propoxy, isopropoxy, n-butoxy, iso-butoxy or tert-butoxy.

Unsubstituted, branched or unbranched $C_1$–$C_{10}$-alkyl radicals which may be mentioned for $R^3$, $R^4$ or $R^5$ are, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl -1-methylpropyl, 1-ethyl-2-methylpropyl, n-heptyl, n-octyl, n-nonyl or n-decyl. Methyl, ethyl, n-propyl, n-butyl, i-propyl or i-butyl are preferred. Substituted $C_1$–$C_{10}$-alkyl radicals which may be mentioned by way of example are the corresponding substituted $C_1$–$C_{10}$-alkyl radicals having the substituents described below.

Unsubstituted, branched or unbranched $C_2$–$C_{10}$-alkenyl radicals which may be mentioned for $R^3$, $R^4$ or $R^5$ are, for example, ethenyl (vinyl), propenyl, 1-butenyl, 2-butenyl, 3-butenyl, 2-methylpropenyl, 1-pentenyl, 2-pentenyl, 3-pentenyl, 4-pentenyl, 1-methyl-1-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl. Substituted $C_2$–$C_{10}$-alkenyl radicals which may be mentioned by way of example are the corresponding substituted $C_2$–$C_{10}$-alkenyl radicals having the substituents described below.

Unsubstituted, branched or unbranched $C_2$–$C_{10}$-alkynyl radicals which may be mentioned for $R^3$, $R^4$ or $R^5$ are, for example, ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the higher homologs of this series. Substituted $C_2$–$C_{10}$-alkynyl radicals which may be mentioned by way of example are the corresponding substituted $C_2$–$C_{10}$-alkynyl radicals having the substituents described below.

Unsubstituted, branched or unbranched $C_1$–$C_{10}$-alkoxy radicals which may be mentioned for $R^3$, $R^4$ or $R^5$ are, for example, methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, hexyloxy, heptyloxy, octyloxy, nonyloxy or decyloxy and their branched-chain homologs. Substituted $C_1$–$C_{10}$-alkoxy radicals which may be mentioned by way of example are the corresponding substituted $C_1$–$C_{10}$-alkoxy radicals having the substituents described below.

Unsubstituted, branched or unbranched $C_2$–$C_{10}$-alkenyloxy radicals which may be mentioned for $R^3$, $R^4$ or $R^5$ are, for example, ethenyloxy, propenyloxy, 1-butenyloxy, 2-butenyloxy, 3-butenyloxy, 2-methylpropenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy, 1-ethyl-2-methyl-2-propenyloxy, 1-heptenyloxy, 2-heptenyloxy, 3-heptenyloxy, 4-heptenyloxy, 5-heptenyloxy, 6-heptenyloxy, 1-octenyloxy, 2-octenyloxy, 3-octenyloxy, 4-octenyloxy, 5-octenyloxy, 6-octenyloxy, 7-octenyloxy, 1-nonenyloxy, 2-nonenyloxy, 3-nonenyloxy, 4-nonenyloxy, 5-nonenyloxy, 6-nonenyloxy, 7-nonenyloxy, 8-nonenyloxy, 1-decenyloxy, 2-decenyloxy, 3-decenyloxy, 4-decenyloxy, 5-decenyloxy, 6-decenyloxy, 7-decenyloxy, 8-decenyloxy or 9-decenyloxy. Substituted $C_2$–$C_{10}$-alkenyloxy radicals which may be mentioned by way of example are the corresponding substituted $C_2$–$C_{10}$-alkenyloxy radicals having the substituents described below.

Unsubstituted, branched or unbranched $C_2$–$C_{10}$-alkynyloxy radicals which may be mentioned for $R^3$, $R^4$ or $R^5$ are, for example, ethynyloxy, prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methyl-but-1-yn-3-yloxy, 3-methyl-but-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yl, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy and the higher homologs of this series. Substituted $C_2$–$C_{10}$-alkynyloxy radicals which may be mentioned by way of example are the corresponding substituted $C_2$–$C_{10}$-alkynyloxy radicals having the substituents described below.

Unsubstituted, branched or unbranched $C_3$–$C_{10}$-cycloalkyl radicals which may be mentioned for $R^3$, $R^4$ or $R^5$ are, for example, cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals can also contain heteroatoms such as S, N and O in the ring. Substituted $C_3$–$C_{10}$-cycloalkyl radicals which may be mentioned by way of example are the corresponding substituted $C_3$–$C_{10}$-cycloalkyl radicals having the substituents described below.

Unsubstituted, branched or unbranched $C_3$–$C_{10}$-cycloalkyloxy radicals which may be mentioned for $R^3$, $R^4$ or $R^5$ are, for example, cyclopropyloxy, cyclobutyloxy, cyclopentyloxy, cyclohexyloxy, cycloheptyloxy, 1-methylcyclopropyloxy, 1-ethylcyclopropyloxy, 1-propylcyclopropyloxy, 1-butylcyclopropyloxy, 1-pentylcyclopropyloxy, 1-methyl-1-butylcyclopropyloxy, 1,2-dimethylcyclopropyloxy, 1-methyl-2-ethylcyclopropyloxy, cyclooctyloxy, cyclononyloxy or cyclodecyloxy. The cycloalkyloxy radicals can also contain further heteroatoms such as S, N and O in the ring. Substituted $C_3$–$C_{10}$-cycloalkyloxy radicals which may be mentioned by way of example are the corresponding substituted $C_3$–$C_{10}$-cycloalkyloxy radicals having the substituents described below.

Unsubstituted, branched-chain or unbranched-chain $C_7$–$C_{16}$-alkylaryl radicals which may be mentioned for $R^3$, $R^4$ or $R^5$ are, for example, methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl. Substituted $C_7$–$C_{16}$-alkylaryl radicals which may be mentioned by way of example are the corresponding substituted $C_7$–$C_{16}$-alkylaryl radicals having the substituents described below.

Unsubstituted, branched-chain or unbranched-chain $C_5$–$C_{18}$-alkylheteroaryl radicals which may be mentioned for $R^3$, $R^4$ or $R^5$ are, for example, $C_4$–$C_{12}$-heteroaryl radicals, as described above for X, substituted with $C_1$–$C_6$-alkyl radicals, as described above for $R^2$. Substituted C5–$C_{18}$-alkylheteroaryl radicals which may be mentioned by way of example are the corresponding substituted $C_5$–$C_{18}$-alkylheteroaryl radicals having the substituents described below.

Unsubstituted or substituted $C_6$–$C_{14}$-aryl radicals or $C_4$–$C_{12}$-heteroaryl radicals for $R^3$, $R^4$ or $R^5$ which may be mentioned by way of example are, for example, the $C_6$–$C_{14}$-aryl radicals and $C_4$–$C_{12}$-heteroaryl radicals described above for X, which can optionally be substituted by one or more of the substituents described below or further saturated or unsaturated nonaromatic rings or ring systems. Phenyl, methoxyphenyl, p-chlorophenyl and furyl or the corresponding substituted compounds are preferred.

Unsubstituted olefinic or aromatic acyl radicals are understood for $R^3$, $R^4$ or $R^5$ as meaning $C_1$–$C_{15}$-acyl radicals, such as $C_1$–$C_4$-alkylacyl radicals, such as formyl, acetyl, propionyl or butyryl or $C_7$–$C_{15}$-arylacyl radicals such as benzoyl or naphthoyl. Substituted acyl radicals which may be mentioned by way of example are the corresponding substituted acyl radicals having the substituents described below.

Possible substituents of the radicals of $R^3$, $R^4$ and $R^5$ mentioned are in principle all conceivable substituents, for example one or more substituents such as halogen, such as fluorine, chlorine, bromine or iodine, or substituents such as cyano, nitro, amino, hydroxyl, alkyl, aryl, cycloalkyl, aryl, heteroaryl, alkoxy, benzyloxy, phenyl or benzyl.

$R^6$ is hydrogen or an unsubstituted or substituted, branched or unbranched $C_1$–$C_6$-alkyl, $C_1$–$C_4$-alkoxy, $C_3$–$C_6$-cycloalkyl, $C_6$–$C_{14}$-aryl or $C_4$–$C_{12}$-heteroaryl radical.

Unsubstituted $C_1$–$C_6$-alkyl radicals which may be mentioned for $R^6$ are, for example, the unsubstituted $C_1$–$C_6$-alkyl radicals described above for $R^2$, preferably methyl or ethyl. Substituted $C_1$–$C_6$-alkyl radicals which may be mentioned by way of example are the corresponding substituted $C_1$–$C_6$-alkyl radicals having the substituents described below, preferably chloromethyl, 2-chloroethyl or methoxymethyl.

Unsubstituted $C_1$–$C_4$-alkoxy radicals which may be mentioned for $R^6$ are, for example, the unsubstituted $C_1$–$C_4$-alkoxy radicals described above for $R^2$, preferably methoxy or ethoxy. Substituted $C_1$–$C_4$-alkoxy radicals which may be mentioned by way of example are the corresponding substituted $C_1$–$C_4$-alkoxy radicals having the substituents described below, such as chloromethoxy.

Unsubstituted $C_3$–$C_6$-cycloalkyl radicals which may be mentioned by way of example for $R^6$ are, for example, the unsubstituted $C_3$–$C_6$-cycloalkyl radicals described above for $R^2$, preferably cyclopentyl or cyclohexyl. The cycloalkyl radicals can also contain heteroatoms such as S, N and O in the ring. Substituted $C_3$–$C_6$-cycloalkyl radicals which may be mentioned by way of example are the corresponding substituted $C_3$–$C_6$-cycloalkyl radicals having the substituents described below.

Unsubstituted $C_6$–$C_{14}$-aryl radicals or $C_4$–$C_{12}$-heteroaryl radicals which may be mentioned for $R^6$ are, for example, the $C_6$–$C_{14}$-aryl radicals and $C_4$–$C_{12}$-heteroaryl radicals described above for X, preferably phenyl, naphthyl or furyl. Substituted $C_6$–$C_{14}$-aryl radicals and $C_4$–$C_{12}$-heteroaryl radicals which may be mentioned by way of example are the corresponding substituted $C_6$–$C_{14}$-aryl radicals and $C_4$–$C_{12}$-heteroaryl radicals having the substituents described below, preferably p-chlorophenyl or p-methoxyphenyl.

Possible substituents of the radicals of $R^6$ mentioned are, for example, one or more substituents such as halogen, such as fluorine, chlorine, bromine or iodine, preferably chlorine or substituents such as cyano, nitro, amino or hydroxyl or substituents such as $C_1$–$C_6$-alkyl, or $C_1$–$C_4$-alkoxy, as described above for $R^2$ in each case.

$R^7$ is hydrogen or an unsubstituted or substituted, branched or unbranched $C_1$–$C_6$-alkyl, $C_1$–$C_4$-alkoxy or $C_3$–$C_6$-cycloalkyl radical.

Unsubstituted $C_1$–$C_6$-alkyl radicals which may be mentioned for $R^7$ are, for example, the unsubstituted $C_1$–$C_6$-alkyl radicals described above for $R^2$, preferably methyl or ethyl. Substituted $C_1$–$C_6$-alkyl radicals which may be mentioned by way of example are the corresponding substituted $C_1$–$C_6$-alkyl radicals having the substituents described below, preferably chloromethyl, 2-chloroethyl or methoxymethyl.

Unsubstituted $C_1$–$C_4$-alkoxy radicals which may be mentioned for $R^7$ are, for example, the unsubstituted $C_1$–$C_4$-alkoxy radicals described above for $R^2$, preferably methoxy or ethoxy. Substituted $C_1$–$C_4$-alkoxy radicals which may be mentioned by way of example are the corresponding substituted $C_1$–$C_4$-alkoxy radicals having the substituents described below, such as chloromethoxy.

Unsubstituted $C_3$–$C_6$-cycloalkyl radicals which may be mentioned for $R^7$ are, for example, the unsubstituted $C_3$–$C_6$-cycloalkyl radicals described above for $R^2$, preferably cyclopentyl or cyclohexyl. The cycloalkyl radicals can also contain heteroatoms such as S, N and O in the ring. Substituted $C_3$–$C_6$-cycloalkyl radicals which may be mentioned by way of example are the corresponding substituted $C_3$–$C_6$-cycloalkyl radicals having the substituents described below.

Possible substituents of the radicals of $R^7$ mentioned are, for example, one or more substituents such as halogen, such as fluorine, chlorine, bromine or iodine, preferably chlorine, or substituents such as cyano, nitro, amino or hydroxyl, or substituents such as $C_1$–$C_6$-alkyl or $C_1$–$C_4$-alkoxy, such as described above for $R^2$ in each case.

In this particularly preferred embodiment of the process according to the invention, the stereoisomeric carboxylic acid esters of the general formula (I) are prepared by reacting a racemic carboxylic acid ester of the general formula II

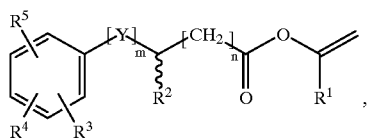

(II)

where
R¹ is hydrogen or $C_1$–$C_4$-alkyl,
with a racemic alcohol of the general formula III

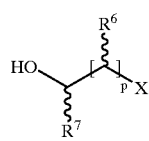

(III)

in the presence of a carboxyl ester hydrolase (EC 3.1.1). R¹ is hydrogen or $C_1$–$C_4$-alkyl, such as methyl, ethyl, propyl, iso-propyl, n-butyl, iso-butyl, tert-butyl, preferably hydrogen or methyl.

Preferred racemic carboxylic acid esters of the general formula II which are particularly highly suitable for the process according to the invention are racemic carboxylic acid esters of the general formula IIa

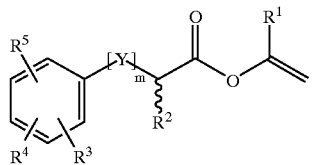

(IIa)

where the variable m and the radicals Y, R², R³, R⁴ and R⁵ have the meanings described above and R¹ is hydrogen or methyl, such as, for example
vinyl (RS)-2-phenylpropionate,
1-methylvinyl (RS)-2-phenylpropionate,
vinyl (RS)-2-phenylbutanoate,
1-methylvinyl (RS)-2-phenylbutanoate,
vinyl (RS)-2-(4-chlorophenyl)propionate,
1-methylvinyl (RS)-2-(4-chlorophenyl)propionate,
vinyl (RS)-2-(4-chlorophenyl)butanoate,
1-methylvinyl (RS)-2-(4-chlorophenyl)butanoate,
vinyl (RS)-2-(4-methylphenyl)propionate,
1-methylvinyl (RS)-2-(4-methylphenyl)propionate,
vinyl (RS)-2-(4-methylphenyl)butanoate,
1-methylvinyl (RS)-2-(4-methylphenyl)butanoate
vinyl (RS)-2-(4-isobutylphenyl)propionate,
1-methylvinyl (RS)-2-(4-isobutylphenyl)propionate,
vinyl (RS)-2-(4-isobutylphenyl)butanoate,
1-methylvinyl (RS)-2-(4-isobutylphenyl)butanoate,
vinyl (RS)-2-(4-benzoylphenyl)propionate,
1-methylvinyl (RS)-2-(4-benzoylphenyl)propionate,
vinyl (RS)-2-(4-benzoylphenyl)butanoate,
1-methylvinyl (RS)-2-(4-benzoylphenyl)butanoate,
vinyl (RS)-2-(6-methoxy-2-naphthyl)propionate,
1-methylvinyl (RS)-2-(6-methoxy-2-naphthyl)propionate,
vinyl (RS)-2-(6-methoxy-2-naphthyl)butanoate,
1-methylvinyl (RS)-2-(6-methoxy-2-naphthyl)butanoate,
vinyl (RS)-2-benzylpropionate,
1-methylvinyl (RS)-2-benzylpropionate,
vinyl (RS)-2-benzylbutanoate,
1-methylvinyl (RS)-2-benzylbutanoate,
vinyl (RS)-2-(4-chlorobenzyl)propionate,
1-methylvinyl (RS)-2-(4-chlorobenzyl)propionate,
vinyl (RS)-2-(4-chlorobenzyl)butanoate,
1-methylvinyl (RS)-2-(4-chlorobenzyl)butanoate,
vinyl (RS)-2-phenoxypropionoate,
1-methylvinyl (RS)-2-phenoxypropionoate,
vinyl (RS)-2-(4-chlorophenoxy)-propionate,
1-methylvinyl (RS)-2-(4-chlorophenoxy)propionate,
vinyl (RS)-2-(2,4-dichlorophenoxy)propionate,
1-methylvinyl (RS)-2-(2,4-dichlorophenoxy)propionate,
vinyl (RS)-2-(3-chlorophenoxy)propionate or
1-methylvinyl (RS)-2-(3-chlorophenoxy)propionate.

In the case of preferred racemic alcohols of the general formula III which are particularly highly suitable for the process according to the invention, the radical X is a substituted or unsubstituted $C_2$–$C_{10}$-alkenyl, $C_2$–$C_{10}$-alkynyl, $C_4$–$C_{12}$-hetaryl or $C_6$–$C_{14}$-aryl radical, while the variable p and the radicals R⁶ and R⁷ have the meanings described above. Particularly preferred racemic alcohols of the general formula III are racemic alcohols of the formula IIIa

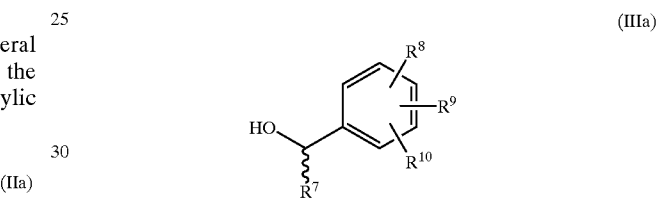

(IIIa)

where R⁷ has the meaning described above and R⁸, R⁹ and R¹⁰ independently of one another have the meanings described above for R³, R⁴ and R⁵.

Those which may be mentioned by way of example are
(RS)1-phenylethanol, (RS)1-phenylpropanol,
(RS)1-(4-chlorophenyl)ethanol, (RS)1-(4-chlorophenyl)propanol,
(RS)2-chloro-1-phenylethanol, (RS)3-chloro-1-phenylpropanol,
(RS)2-chloro-1-(4-chlorophenyl)ethanol,
(RS)3-chloro-1-(4-chlorophenyl)propanol,
(RS)2-chloro-1-(3-chlorophenyl)ethanol,
(RS)3-chloro-1-(3-chlorophenyl)propanol,
(RS)2-chloro-1-(2-chlorophenyl)ethanol,
(RS)3-chloro-1-(2-chlorophenyl)propanol,
(RS)1- (4-nitrophenyl)ethanol, (RS)1- (4-nitrophenyl)propanol,
(RS)1-naphthylethanol, (RS)1-naphthylpropanol,
(RS)1-(6-methoxynaphthyl)ethanol,
(RS)1-(6-methoxynaphthyl)propanol,
(RS)2-chloro-1-naphthylethanol, (RS)3-chloro-1-naphthylpropanol,
(RS)2-chloro-1-(6-methoxynaphthyl)ethanol,
(RS)3-chloro-1-(6-methoxynaphthyl)propanol,
(RS)1-(4-methylphenyl)ethanol, (RS)1-(4-methylphenyl)propanol,
(RS)2-chloro-1-(4-methylphenyl)ethanol,
(RS)3-chloro-1-(4-methylphenyl)propanol,
(RS)1-(4-ethylphenyl)ethanol, (RS)1-(4-ethylphenyl)propanol,
(RS)2-chloro-1-(4-ethylphenyl)ethanol,
(RS)3-chloro-1-(4-ethylphenyl)propanol,
(RS)1-(4-methoxyphenyl)ethanol, (RS)1-(4-methoxyphenyl)propanol, (RS)2-chloro-1-(4-methoxyphenyl)ethanol,
(RS)3-chloro-1-(4-methoxyphenyl)propanol,
(RS)1-(2-methylphenyl)ethanol, (RS)1-(2-methylphenyl)propanol,
(RS)2-chloro-1-(2-methylphenyl)ethanol,
(RS)3-chloro-1-(2-methylphenyl)propanol,
(RS)1-(2-ethylphenyl)ethanol, (RS)1-(2-ethylphenyl)propanol,
2-chloro-1-(2-ethylphenyl)ethanol,
(RS)3-chloro-1-(2-ethylphenyl)propanol,
(RS)1-(2-methoxyphenyl)ethanol, (RS)1-(2-methoxyphenyl)propanol,
2-chloro-1-(2-methoxyphenyl)ethanol,
(RS)3-chloro-1-(2-methoxyphenyl)propanol,
(RS)1-(3-methylphenyl)ethanol, (RS)1-(3-methylphenyl)propanol,
(RS)2-chloro-1-(3-methylphenyl)ethanol,
(RS)3-chloro-1-(3-methylphenyl)propanol,
(RS)1-(3-ethylphenyl)ethanol, (RS)1-(3-ethylphenyl)propanol,
(RS)2-chloro-1-(3-ethylphenyl)ethanol,
(RS)3-chloro-1-(3-ethylphenyl)propanol,
(RS)1-(3-methoxyphenyl)ethanol, (RS)1-(3-methoxyphenyl)propanol,
(RS)2-chloro-1-(3-methoxyphenyl)ethanol,
(RS)3-chloro-1-(3-methoxyphenyl)propanol or
(RS)1-(1,3)-benzodioxolethanol.

In the process according to the invention, the racemic alcohol and the racemic carboxylic acid ester are advantageously employed in equimolar amounts.

In principle, all carboxyl ester hydrolases (EC 3.1.1), such as microbial, animal or plant carboxyl ester hydrolases, are suitable for the process according to the invention. The carboxyl ester hydrolases can be used as free enzymes or as enzyme formulations, for example in immobilized form. The reaction can also be carried out in the presence of the entire organisms or crude extracts of the organisms. Advantageously, carboxyl esterases (esterases (EC 3.1.1.1)) or lipases (EC 3.1.1.3) are used as carboxyl ester hydrolases. Bacterial, fungal, animal or plant lipases or carboxyl esterases are preferably used. Those which may be mentioned by way of example as carboxyl esterases are carboxyl esterases from *Bacterium subtilis, Bacterium stearothermophilus, Bacterium thermoglucosidasius, Candida lipolytica, Mucor miehei*, equine liver, porcine liver, *Saccharomyces cerevisiae, Thermoanaerobium brocki* or *Electrophorus electricus*.

Lipases are particularly preferably used. Suitable lipases are porcine pancreatic lipase (PPL) or wheatgerm lipase and also bacterial or fungal lipases which are isolable from the genera Aspergillus, Arthrobacter, Alcaligenes, Bacillus, Brevibacterium, Pseudomonas, Burkholderia, Chromobacterium, Candida, Fusarium, Geotrichum, Humicola, Mucor, Pichia, Penicillium, Rhizomucor, Rhizopus or Thermus. Those which are particularly advantageously suitable are lipases from the genera and species Arthrobacter sp., Alcaligenes sp., *Bacillus cereus, Bacillus subtilis, Bacillus coagulans, Burkholderia plantarii, Brevibacterium ammoniagenes, Pseudomonas aeruginosa, Pseudomonas cepacia, Pseudomonas fluorescens, Pseudomonas putida*, Pseudomonas sp., *Chromobacterium viscosum, Aspergillus niger, Aspergillus oryzae, Candida antarctica, Candida cylindracea, Candida rugosa, Candida lipolytica, Candida utilis, Fusarium solani, Geotrichum candidum, Humicola lanuginosa, Mucorjavanicus, Mucorjaponicus, Mucor miehei*, Mucor sp., *Penicillium acylase, Penicillium roquefortii, Pichia miso, Rhizopus nigricans, Rhizopus oryzae, Rhizopus arrhizus, Rhizopus delemar, Rhizopus niveus*, Rhizopus sp., *Rhizomucor miehei, Thermus aquaticus, Thermus flavus* or *Thermus thermophilus*.

Commercially obtainable lipases or formulations of these lipases which are obtainable, for example, from Amano, Novo or Boehringer Mannheim are suitable for the process according to the invention. The preferred lipases are those from Candida antartica, which is obtainable in two isoforms A or B or their mixture, or lipases from Candida cylindracea. These enzymes are suitable as free enzymes or as enzyme formulations, for example as lipase Chirazyme L2 from Boehringer Mannheim or as Novozym 435 from Novo, for the process according to the invention. Candida antartica lipase B (=CAL-B) is particularly suitable.

In the process according to the invention, stereoisomeric carboxylic acid esters are formed, at least one stereoisomer being present in an excess. Advantageously, one stereoisomer is formed in a large excess, so that after reaction has taken place the reaction mixture contains as main products the excess stereoisomer, the unreacted or only slightly reacted carboxylic acid enantiomer and the unreacted or only slightly reacted alcohol enantiomer.

The process according to the invention is advantageously carried out in the presence of at least one organic solvent, but can also be carried out without the presence of a solvent. In this case, the racemic alcohol of the general formula (III) serves as a solvent. Possible solvents are all organic solvents which can increase the starting material and product solubility and positively affect the reaction time and the enantioselectivity. When using an organic solvent, the solvent can exert an effect on the enantioselectivity. Depending on the solvent, the enantioselectivity can be increased or reduced or even reversed. The optimal solvent for the particular starting materials and enzymes can be determined by simple preliminary experiments. Preferably, organic solvents used for the process according to the invention are aprotic solvents such as toluene, hexane or benzene or polar aprotic solvents such as DMSO, DMF or N-methylpyrrolidone.

The process according to the invention can be carried out at temperatures between −50° C. and +100° C. When using thermostable enzymes, even higher reaction temperatures can be achieved (see, for example, Ikeda et al., Molecular cloning of extremely thermostable esterase gene from hyperthermophilic archaean Pyrococcus furiosus in Escherichia coli, Biotechnol. Bioeng., 57, 1998: 624–629). In the region of 0° C. or below, the reaction rate markedly decreases. A reaction in this region is, however, possible in principle, as can be seen from Sakai et al. (Enhancement of the enantioselectivity in lipase-catalysed kinetic resolutions of 3-phenyl-2H-azirine-2-methanol by lowering the temperature to −40 degrees, J. Org. Chem., 62, 1997: 4906–4907). Preferably, the process is carried out between 0° C. and 90° C., particularly preferably between 10° C. and 80° C.

The reaction times up to the establishment of the equilibrium are typically 1 h to 60 h, preferably 2 to 40 h.

The process according to the invention can be carried out continuously or batchwise. To carry out the process continuously, a liquid mobile phase, for example, is led into a reactor through a packed bed of free or immobilized carboxyl ester hydrolase in a manner known per se. The mobile phase can be either a solution of the racemic starting materials in an abovementioned organic solvent or the liquid starting material mixture without solvent. The flow rate is not critical and depends on process technology standpoints such as height, diameter and particle size of the packed bed and on the form of the reactor. Reactors used for the continuous process are preferably the reactors (J. Hagen, Chemische Reaktionstechnik, [Chemical reaction technology] VCH, Weinheim 1992, pp. 165–169) customary for continuous, heterogeneous catalytic processes (fluid/solid reactions). By way of example, fluidized bed reactors and fixed bed reactors, such as tubular reactors, column reactors, full-space reactors, tray reactors, multitube reactors and flat bed contact reactors.

In the batchwise process procedure, the carboxyl ester hydrolase is suspended in a solution of the racemic starting materials in an abovementioned organic solvent or in the liquid starting material mixture with or without organic solvent in a reactor in a manner known per se and the suspension is thoroughly mixed. Reactors used for the batchwise process are preferably the reactors customary for batchwise, heterogeneous catalytic processes (fluid/solid reactions) having a shaking, mixing or stirring device. By way of example, the stirred vessel and embodiments derived therefrom and reaction vessels having a shaking device may be mentioned.

The separation and isolation of the stereoisomeric carboxylic acid ester which is present in the product mixture in an excess after carrying out the process according to the invention can be carried out by physical or chemical purification and separation processes in a manner known per se. By way of example, extraction processes, chromatographic processes, such as, for example, chromatography on silica gel or HPLC on chiral columns, crystallization processes, such as crystallization and recrystallization from organic solvents, such as n-hexane, toluene or methylene chloride, or rectification processes such as distillation may be mentioned.

Moreover, the process according to the invention is suitable for resolution of racemic alcohols and racemic carboxylic acid esters in a one-pot reaction.

The process according to the invention has the following advantages compared with the prior art:

The conversion is increased to about 50% with markedly shorter reaction times.

At the same time, high enantioselectivities and diastereomer excesses are obtained here.

The diastereomer excess in the products obtained can be further increased by recrystallization directly without further purification.

The examples below illustrate the invention:

GENERAL EXPERIMENTAL CONDITIONS

If not described otherwise, the $^1$H-NMR spectra were recorded at 250.1 and 500.1 MHz and the $^{13}$C-NMR spectra at 62.9 and 125.7 MHz in $CDCl_3$ using tetramethylsilane as an internal standard. The signals given in italics correspond to the excess diastereomer. For confirmation of the chemical identity, the carboxylic acid esters were also prepared chemically.

The determination of the absolute configuration and of the enantiomeric and diastereomeric excess was carried out as described below. The enantiomeric excess of the carboxylic acid ester was determined by GC on a heptakis (2,3-di-O-acetyl-6-O-TBDMS)-β-cyclodextrin column (25 m×0.25 mm, Prof. W. A. König, University of Hamburg).

The enantiomeric excess of the alcohol was determined by GC on a heptakis(2,3,6-tri-O-methyl)-β-cyclodextrin column (50 m×0.25 mm, CS-Chromatographie-Service, Langerwehe). The determination of the diastereomeric excess of the carboxylic acid ester and of the conversion was carried out by GC on an Optima 5 column (25 m×0.25 mm; Macherey & Nagel, Düren). The diastereomeric excess was additionally verified by comparison of the signal intensities of the diastereomers in an NMR experiment. The enantiomeric excess of the carboxylic acid and alcohol components of the prepared stereoisomeric carboxylic acid ester was additionally determined after chemical hydrolysis. Hydrolysis was carried out by dissolving the carboxylic acid ester (3 mg) in heptane (200 μl), adding a methanolic potassium hydroxide solution (2N, 90 μl) and subsequently stirring (1 min). Samples from the organic phase, containing the alcohol formed from the alcohol components of the carboxylic acid ester and the carboxylic acid methyl ester formed from the carboxylic acid component, were analyzed by GC by using the chiral columns described above. The enantiomeric excesses were verified by measuring the specific optical rotations on a Perkin Elmer 241 Polarimeter. The absolute configuration was assigned by comparison with the specific rotations of optically pure samples.

The enantioselectivity was presented using the formulae $$E=[\ln\{(1-c)\times(1-ee_s)\}]/[\ln\{(1-c)\times(1+ee_s)\}],$$

or $$E=[\ln\{1-cx(1+ee_p)\}]/[\ln\{1-cx(1-ee_p)\}]$$

in each case for the alcohol and the carboxylic acid components, where c is the conversion, $ee_s$ is the enantiomeric excess of a substrate enantiomer and $ee_p$ is the enantiomeric excess of a product enantiomer (Sih et al., J. Am. Chem. Soc. 1982, 104, 7294–7299).

The immobilized lipase used was, if not described otherwise, lipase from Candida antarctica (SP435) (CAL-B; Chirazyme L-2, c.-f., C2, 5000 U/g) from Boehringer Mannheim, Penzberg. Unless described otherwise, all chemicals were obtained from Fluka, Buchs, Switzerland. The solvents and the lipase were dried over activated molecular sieve (4 Å) before use thereof.

EXAMPLE 1

Preparation of the Racemic Carboxylic Acid Esters
1.1 Preparation of the Racemic Carboxylic Acid Vinyl Esters
General Working Procedure The racemic carboxylic acid vinyl esters were prepared according to the method described by Wang et al. (J. Am. Chem. Soc. 1988, 110, 7200). 500 mg of the carboxylic acid and $HgOAc_2$ (70 mg, 0.22 mmol) were dissolved in vinyl acetate (10 ml). The solution was stirred at room temperature (23° C.) for 30 min, then 0.1 ml of $H_2SO_4$ (conc.) was added, and the solution was refluxed for 6 hours and cooled to room temperature. 400 mg of NaOAc were then added to quench the catalyst. The solution was filtered and concentrated. The crude products were then purified by means of silica gel chromatography (petroleum ether: $Et_2O$, 20:1). All vinyl esters were obtained as colorless liquids which needed no further purification. Optically pure vinyl esters were synthesized in relatively small amounts using 60 to 120 mg of optically pure carboxylic acids.

1.1.1 Vinyl (RS)-2-phenylbutyrate ((RS)IIaa)

Preparation was carried out according to the method described above using 500 mg (=3.05 mmol) of the corresponding racemic carboxylic acid [(RS)2-phenylbutyric acid]. 290 mg of (RS)IIaa (1.52 mmol, 50%) were obtained.

Analytical Data

C, 75.80; H, 7.41.; calc. for $C_{12}H_{14}O_2$: C, 75.76; H, 7.42;

$^1$H-NMR (500.1 MHz; CDCl$_3$) δ[ppm]=0.91 (t, J=7.4, 3H), 1.80–2.16 (m, 2H), 3.51 (t, J=7.7, 1H), 4.54 (dd, J=6.32, 1.6, 1H), 4.85 (dd, J=14.0, 1.7, 1H), 7.23–7.34 (m, 6H);

$^{13}$C-NMR (125.8 MHz; CDCl$_3$) δ[ppm]=12.08, 26.62, 53.17, 97.90, 127.41, 128.00, 128.67, 138.28, 141.32, 171.12;

IR (KBr)/cm$^{-1}$: 3080w, 3050w, 3015w, 2955vs, 2920s, 2860w, 1750vs, 1640vs, 1595w, 1475s, 1447s, 1130br, 860s, 720s, 680vs.

1.1.2 Vinyl R-(–)-2-phenylbutyrate ((R-(–)-IIaa)

120 μl of R-(–)-2-phenylbutyric acid (126.6 mg, 0.77 mmol) afforded 44 mg of R-(–)-IIaa (0.23 mmol, 30%); $[α]_D^{22}$ =–23.9° (c 0.664, CHCl$_3$).

1.1.3 Vinyl (RS)-2-phenylpropionate ((RS)IIab)

420 μl of (RS)-2-phenylpropionic acid (460.7 mg, 3.07 mmol) afforded 210 mg of (RS)IIab (1.19 mmol, 39%).

Analytical Data

C, 74.73; H, 6.93; calc. for $C_{11}H_{12}O_2$; C, 74.98; H, 6.86;

$^1$H-NMR (500.1 MHz; CDCl$_3$) δ[ppm]=1.53 (d, J=7.2, 3H), 3.79 (q, J=7.1, 1H), 4.54 (d, J=6.18; 1H), 4.77 (d, J=14.0, 1H), 7.23–7.35 (m, 6H);

$^{13}$C NMR (125.7 MHz; CDCl$_3$) 18.41, 45.26, 97.92, 127.36, 127.52, 128.73, 139.71, 141.36, 171.59;

IR (KBr)/cm$^{-1}$: 3080w, 3050w, 3020s, 2970s, 2920s, 2860w, 1750vs, 1640vs, 1595w, 1485s, 1445s, 1140br, 860s, 715s, 680vs.

1.1.4 Vinyl R-(–)-2-phenylpropionate ((R)-(–)-IIab)

60 μl of R-(–)-2-phenylpropionic acid (65.8 mg, 0.44 mmol) afforded 18 mg of (R)-(–)-IIab (0.10 mmol, 23%) $[α]_D^{22}$ =–34.6° (c 0.900, EtOH).

1.1.5 Vinyl (RS)-3-phenylbutyrate ((RS)IIb)

500 mg of (RS)-3-phenylbutyric acid (3.05 mmol) afforded 300 mg of (RS)IIb (1.58 mmol, 52%):

Analytical Data

C, 75.63; H, 7.68; calc. for $C_{12}H_{14}O_2$: C, 75.76; H, 7.42;

$^1$H NMR (250.1 MHz; CDCl$_3$) δ1.25 (d, J=7.0, 3H), 2.59 (m, 2H), 3.24 (m, 1H), 4.47 (dd, J=6.3, 1.5, 1H), 4.77 (dd, J=14.0, 1.5, 1H), 7.13–7.27 (m, 6H);

$^{13}$C NMR (62.9 MHz; CDCl$_3$) 21.82, 36.27, 42.60, 97.76, 126.63, 126.78, 128.66, 141.18, 145.41, 169.48;7

IR (KBr)/cm$^{-1}$: 3070w, 3050w, 3010s, 2950s, 2910w, 2860w, 1750vs, 1640vs, 1595w, 1485s, 1445s, 1140br, 860s, 745s, 680vs.

1.1.6 Vinyl R-(–)-3-phenylbutyrate (R-(–)-IIb)

120 μl of R-(–)-3-phenylbutyric acid (128.3 mg, 0.78 mmol) afforded 29 mg of R-(–)-IIb (0.15 mmol, 19%) $[α]_D^{22}$ =–21.20° (c 1.543, 1.4-dioxane).

EXAMPLE 2

Lipase-catalyzed Reaction of Racemic Carboxylic Acid Esters with Racemic Alcohols

EXAMPLE 2.1

Lipase-catalyzed Reaction of Racemic Carboxylic Acid Vinyl Esters with Racemic Alcohols General Working Procedure The racemic carboxylic acid vinyl ester (0.65 mmol) and the racemic alcohol (0.65 mmol) were dissolved in 6 ml of toluene and the solution was stirred at 40° C. The reaction was started by addition of 300 mg of CAL-B lipase. Samples were taken from the reaction, diluted with toluene and analyzed by gas chromatography (GC) using the Optima 5 column. At 50% conversion, the reaction was ended by removing the lipase by centrifugation. The product and unreacted substrate were purified by flash chromatography on silica gel.

2.1.1 Preparation of (R)-1-phenethyl (R)-2-phenylbutyrate ((R,R)Ia) by lipase-catalyzed reaction of vinyl (RS)-2-phenylbutyrate ((RS)IIaa) with (RS)-1-phenylethanol ((RS) IIIaa)

Scheme 1 shows the reaction. The main products present after the reaction are (R)-1-phenethyl (R)-2-phenylbutyrate ((R,R)Ia), the ethanal tautomerized from the leaving group vinylethanol, and the unreacted substrates vinyl (S)-(–)-2-phenylbutyrate ((S)-(+)-IIaa) and (S)-1-phenylethanol ((S)-IIIaa).

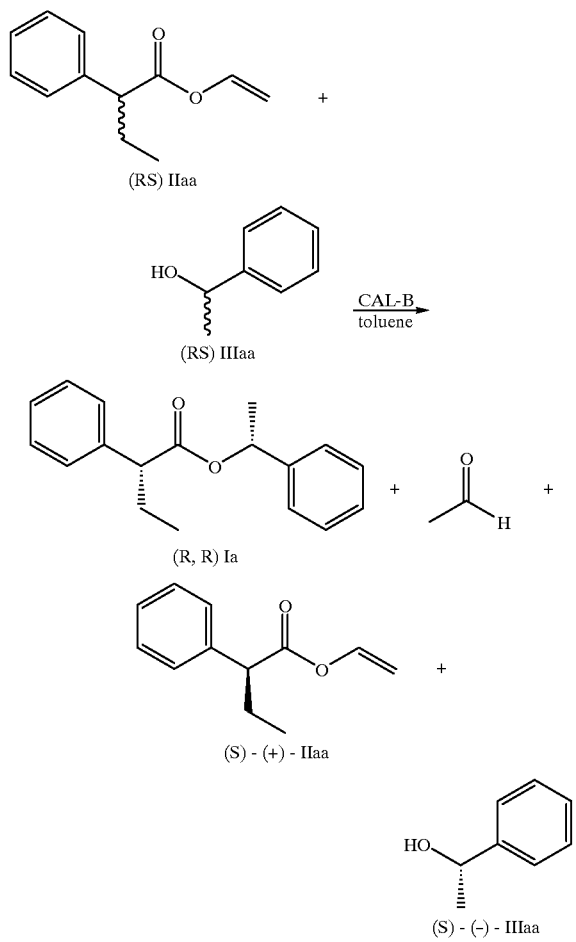

Scheme 1

Carrying out the reaction according to the general working procedure described above yielded, after a reaction time of 35 hours, 70 mg of (R,R)Ia (0.26 mmol, 40% yield, >98%ee (alcohol component (R)-(+)-IIIaa after hydrolysis), 56% de (GC)) as a colorless liquid. Unreacted vinyl ester (S)-(+)-IIaa: 50 mg, 0.26 mmol, 41% yield, 58%ee, $[α]_D^{22}$=+14.9° (c 1.35, CHCl$_3$) Unreacted alcohol (S)-(–)-IIIa: 31 mg, 0.25 mmol, 39% yield, 94%ee, $[a]^{22}$D=–36.8° (c=1.1, MeOH).

The results and the E values calculated therefrom are compiled in Table 1.

Analytical Data of (R,R)Ia

Elemental analysis: C 80.42, H 7.53, calc. for $C_{18}H_{20}O_2$: C 80.56, H 7.51, O 11.92.

$^1$H-NMR (500.1 MHz; CDCl$_3$): δ1.06 (3H, t, $J_{3,4}$ 7.4, 4-H), 1.10 (3H, t, $J_{3,4}$ 7.3, 4-H), 1.63 (3H, d, $J_{1',2'}$ 6.7, 2'-H), 1.71 (3H, d, $J_{1',2'}$, 6.5, 2'-H), 1.98–2.34 (2H, m, 3-H); 3.69 (1H, m, 2-H), 6.06 (1H, q, $J_{1',2'}$, 6.6), 7.31–7.53 (10 H, m, Ph-H);

$^{13}$C-NMR (125.8 MHz; CDCl$_3$): δ12.54 (4-C), 22.36, 22.75 (2'-C), 26.90, 27.07 (3-C), 54.02, 54.09 (2-C), 72.78, 72.90 (1'-C), 126.10, 126.42, 127.47, 127.50, 127.95, 128.17, 128.38, 128.46, 128.69, 128.83, 128.86, 128.89, 139.38, 139.51, 142.04, 142.10 (Ph-C), 173.72, 173.72 (1-C);

IR (KBr) [cm$^{-1}$]: 2950m, 2910m, 1740s, 1485m, 1445m, 1190s, 1150s, 1050s, 1015m, 740m, 680m;

2.1.2 Preparation of (R)-1-phenethyl (R)-2-phenylpropionate ((R,R)Ib) by lipase-catalyzed reaction of vinyl (RS)-2-phenylpropionate ((RS)IIab) with (RS)-1-phenylethanol ((RS)IIIaa)

Scheme 2 shows the reaction. The main products present after the reaction are (R)-1-phenethyl (R)-2-phenylpropionate ((R,R)Ib), the ethanal tautomerized from the leaving group vinylethanol, and the unreacted substrates vinyl (S)-(+)-2-phenylpropionate ((S)-(+)-IIaa) and (S)-(−)-1-phenylethanol ((S)-(−)-IIIaa).

Scheme 2

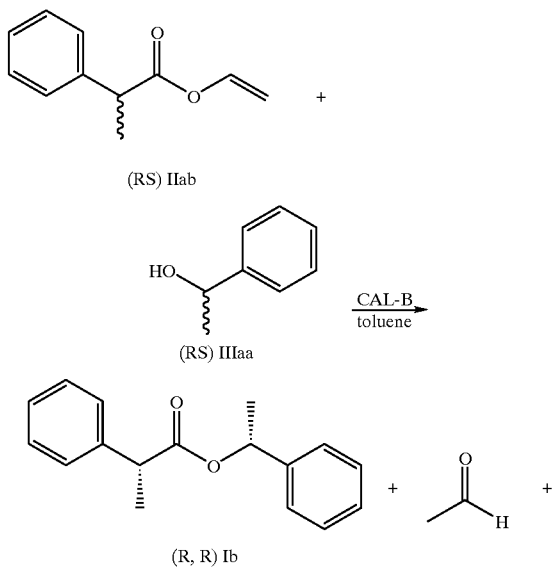

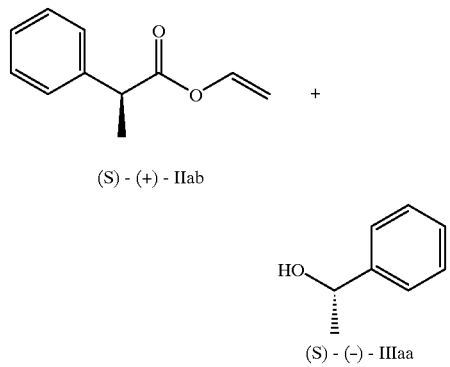

Carrying out the reaction according to the general working procedure described above yielded, after a reaction time of 2.5 hours, 74 mg of (R,R)Ib (0.29 mmol, 45% yield, >98%ee (alcohol components (R)-(+)-IIIaa after hydrolysis), 64% de (GC), m.p. 92 to 93° C.). Recrystallization from n-hexane yielded ((R,R)Ib) in 98% de (GC; >95% de, $^1$H NMR). Unreacted vinyl ester (S)-(+)-IIab: 42 mg, 0.24 mmol, 36% yield, 67%ee, $[\alpha]^{22}_D$=+24.9° (c=1.19, EtOH); unreacted alcohol (S)-(−)-IIIaa: 33 mg, 0.27 mmol, 41% yield, >98%ee, $[\alpha]^{22}_D$=−40.8° (c=1.3, MeOH).

The results and the E values calculated therefrom are compiled in Table 1.

Analytical Data of (R,R)Ib

Elemental analysis: C 80.21, H 7.21; calc. for $C_{17}H_{18}O_2$: C 80.28, H 7.13, O 12.58.

$^1$H NMR (250.1 MHz; CDCl$_3$) : δ1.48 (3H, d, $J_{1',2'}$, 6.6, 2'-H), 1.49 (3H, d, $J_{2,3}$ 7.2, 3-H), 3.75 (1H, q, $J_{2,3}$=7.2, 2-H), 5.85 (1H, q, $J_{1',2'}$=6.6, 1'-H), 7.06–7.31 (10H, m, Ph-H);

$^{13}$C NMR (62.9 MHz; CDCl$_3$) δ18.47 (3-C), 22.48 (2'-C), 45.86 (2-C), 72.59 (1'-C), 125.80, 127.16, 127.73, 128.42, 128.66, 140.57, 141.81 (Ph-C), 173.67 (1-C);

IR (KBr) [cm$^{-1}$]: 2960m, 1725s, 1325m, 1190s, 1160s, 1045m, 740m, 680s.

TABLE 1

| Example | Reaction time in [h] | Conversion in [%] | Enantiomeric excess in [% ee] | | | Enantioselectivity E | | Diastereomeric excess in [% de]$^{(f)}$ |
|---|---|---|---|---|---|---|---|---|
| | | | S-II$^{(a)}$ | S-III$^{(b)}$ | R-III$^{(c)}$ | Acid$^{(d)}$ | Alcohol$^{(e)}$ | |
| 2.1.1 | 35 | 50 | 58 | 94 | 98 | 7 | >100 | 56 |
| 2.1.2 | 2.5 | 50 | 67 | 98 | 98 | 10 | >100 | 64 (98)$^{(g)}$ |

Enantiomeric excess
[a] of the remaining (S)-carboxylic acid vinyl ester of the formula II
[b] of the remaining (S)-alcohol of the formula III
[c] of the (R)-alcohol component of the carboxylic acid ester stereoisomers of the formula I formed after hydrolysis
Enantioselectivity E compared with
[d] the carboxylic acid component
[e] the alcohol component
[f] diastereomeric excess of the sum of the (R, R) and (S, S) stereoisomers compared with the sum of the (R, S) and (S, R) stereoisomers
[g] after recrystallization from n-hexane

We claim:

1. A process for the preparation of stereoisomeric carboxylic acid esters of the general formula I

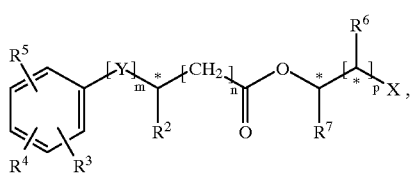  (I)

where the substituents and variables have the meanings
* is a possible chiral center,
n, m, p independently of one another are 0 or 1,
X is an unsubstituted or F—, Cl—, Br—, I—, $NO_2$— or $C_1$–$C_4$-alkoxy-substituted $C_1$–$C_{10}$-alkyl, $C_2$–$C_{10}$-alkenyl, $C_2$–$C_{10}$-alkynyl or $C_3$–$C_8$-cycloalkenyl, $C_6$–$C_{14}$-aryl, $C_7$–$C_{16}$-alkylaryl, $C_8$–$C_{16}$-alkenylaryl, $C_8$–$C_{16}$-alkynylaryl, $C_7$–$C_{18}$-arylalkyl, $C_8$–$C_{18}$-arylalkenyl, $C_8$–$C_{18}$-arylalkynyl or $C_4$–$C_{12}$-heteroaryl radical or a substituted $C_6$–$C_{14}$-aryl, $C_7$–$C_{16}$-alkylaryl, $C_8$–$C_{16}$-alkenylaryl, $C_8$–$C_{16}$-alkynylaryl, $C_7$–$C_{18}$-arylalkyl, $C_8$–$C_{18}$-arylalkenyl, $C_8$–$C_{18}$-arylalkynyl or $C_4$–$C_{12}$-heteroaryl radical, where in each case two adjacent aryl substituents can together form a further substituted or unsubstituted aromatic, saturated or partially saturated ring having 5 to 6 atoms in the ring, which can contain one or more heteroatoms such as O, N or S,
Y is —$CH_2$—, —CO—, oxygen or sulfur,
$R^2$ is a substituted or unsubstituted, branched or unbranched $C_1$–$C_6$-alkyl, $C_1$–$C_4$-alkoxy, $C_3$–$C_6$-cycloalkyl, $C_6$–$C_{14}$-aryl or $C_4$–$C_{12}$-heteroaryl radical,
$R^3$, $R^4$, $R^5$ independently of one another are hydrogen, a hydroxyl, halogen, cyano, nitro or amino radical or a substituted or unsubstituted, branched or unbranched $C_1$–$C_{10}$-alkyl, $C_2$–$C_{10}$-alkenyl, $C_2$–$C_{10}$-alkynyl, $C_1$–$C_{10}$-alkoxy, $C_2$–$C_{10}$-alkenyloxy, $C_2$–$C_{10}$-alkynyloxy, $C_3$–$C_{10}$-cycloalkyl, $C_3$–$C_{10}$-cycloalkyloxy, $C_6$–$C_{14}$-aryl, $C_7$–$C_{18}$-alkylaryl, $C_4$–$C_{12}$-heteroaryl or $C_5$–$C_{16}$-alkylheteroaryl radical or a substituted or unsubstituted olefinic or aromatic acyl radical or two adjacent substituents $R^3$, $R^4$ and $R^5$ can together form a further substituted or unsubstituted aromatic, saturated or partially saturated ring having 5 to 6 atoms, which can contain one or more heteroatoms such as O, N or S,
$R^6$ is hydrogen or a substituted or unsubstituted, branched or unbranched $C_1$–$C_6$-alkyl, $C_1$–$C_4$-alkoxy, $C_3$–$C_6$-cycloalkyl, $C_6$–$C_{14}$-aryl or $C_4$–$C_{12}$-heteroaryl radical and
$R^7$ is hydrogen or a substituted or unsubstituted, branched or unbranched $C_1$–$C_6$-alkyl, $C_1$–$C_4$-alkoxy or $C_3$–$C_6$-cycloalkyl radical, where in the case where p=0, $R^7$ is not hydrogen or X and in the case where p=1, either $R^6$ or $R^7$ is hydrogen, but not both are simultaneously hydrogen and in the case where $R^7$=hydrogen, $R^6$ is not X and in the case where $R^7$ is not hydrogen, $R^6$ is hydrogen or X, which comprises reacting a racemic carboxylic acid ester of the general formula II

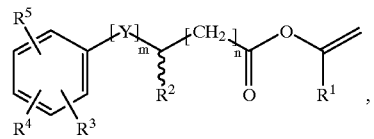  (II)

where
$R^1$ is hydrogen or $C_1$–$C_4$-alkyl,
with a racemic alcohol of the general formula IIII

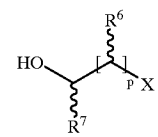  (III)

in the presence of a carboxyl ester hydrolase (EC 3.1.1).

2. A process as claimed in claim 1, wherein the racemic alcohol and the racemic carboxylic acid ester are employed in equimolar amounts.

3. A process as claimed in claim 1, wherein the carboxyl ester hydrolase used is a carboxyl esterase (EC 3.1.1.1) or a lipase (EC. 3.1.1.3).

4. A process as claimed in claim 1, wherein the carboxyl ester hydrolase used is porcine pancreas lipase (PPL), wheatgerm lipase or a bacterial or fungal lipase which is isolable from the genera Aspergillus, Arthrobacter, Alcaligenes, Bacillus, Brevibacterium, Pseudomonas, Burkholderia, Chromobacterium, Candida, Fusarium, Geotrichum, Humicola, Mucor, Pichia, Penicillium, Rhizomucor, Rhizopus or Thermus.

5. A process as claimed in claim 1, wherein the carboxyl ester hydrolase used is *Candida antarctica* lipase (B).

6. A process as claimed in claim 1, wherein the carboxyl ester hydrolase is used as an immobilized enzyme formulation.

7. A process as claimed in claim 1, wherein the process is carried out in the presence of an organic solvent.

* * * * *